United States Patent [19]

Ohshiro et al.

[11] Patent Number: 4,866,170

[45] Date of Patent: Sep. 12, 1989

[54] STABLE HYDRATE OF PENICILLIN DERIVATIVE

[75] Inventors: Susumu Ohshiro, Kawanishi; Masaru Senuma, Takatsuki; Mitsuyoshi Wagatsuma, Urawa, all of Japan

[73] Assignee: Tanabe Seiyaku Co., Ltd., Osaka, Japan

[21] Appl. No.: 98,364

[22] Filed: Sep. 18, 1987

[30] Foreign Application Priority Data

Sep. 24, 1986 [JP] Japan ................... 61-226423

[51] Int. Cl.$^4$ ............................................ C07D 499/68
[52] U.S. Cl. ...................................... 540/335; 540/320; 540/336
[58] Field of Search ................. 540/320, 335, 336

[56] References Cited

U.S. PATENT DOCUMENTS 4,053,609  10/1977  Kawazu et al. .............. 514/197
4,313,875   2/1982  Nakamura et al. ........... 540/322

FOREIGN PATENT DOCUMENTS 1216714  12/1970  United Kingdom .

Primary Examiner—Werren B. Lone
Assistant Examiner—Vera C. Clarke
Attorney, Agent, or Firm—Birch, Stewart, Kolasch & Birch

[57] ABSTRACT

A stable trihydrate of (2S, 5R, 6R)-6-{(2R)-2-[(2R)-2-amino-3-(N-methylcarbamoyl)propionamido]-2-(p-hydroxyphenyl)acetamido}-3,3-dimethyl-7-oxo-4-thia-1-azabicyclo[3.2.0]heptane-2-carboxylic acid and process for preparing the same are disclosed.

1 Claim, 1 Drawing Sheet

STABLE HYDRATE OF PENICILLIN DERIVATIVE

SUMMARY OF THE INVENTION

This invention relatesto a stable hydrate of a penicillin derivative and a process for preparing same. More particularly, it relates to (2S, 5R, 6R)-6- {(2R)-2-[2R)-2-amino-3-(N-methylcarbamoyl)propionamido]-2-(p-hydroxyphenyl)- acetamido}-3,3-dimethyl-7-oxo-4-thia-1-azabicyclo[3.2.0]heptane-2-carboxylic acid trihydrate (hereinafter referred to as ("$N^4$-methyl-D-asparaginylamoxicillin") of the formula:

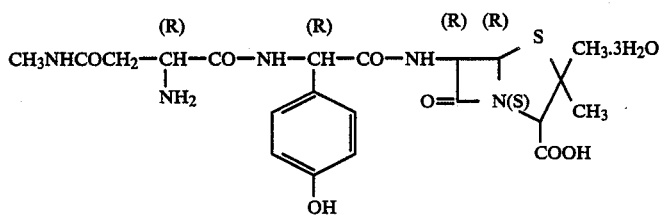

$N^4$-Methyl-D-asparaginylamoxicillin is useful as a chemotherapeutic agent because it shows potent antimicrobial activity against both of gram-positive and gram-negative microorganisms. It has been known that $N^4$-methyl-D-asparaginylamoxicillin can be prepared either (i) by condensing 6-aminopenicillanic acid with D-2-(D-2-amino-3-N-methylcarbamoyl-propionamido)-2-propionamido)-2-p-hydroxyphenylacetic acid, or (ii) by condensing amoxicillin with D-2-amino-3-N-methylcarbamoylpropionic acid (U.S. Pat. No. 4,053,609). It has also been known that pure $N^4$-methyl-D-asparaginylamoxicillin can be obtained as amorphous anhydrate by contacting an aqueous solution of crude $N^4$-methyl-D-asparaginylamoxicillin with a non-polar macroporous adsorption resin, eluting the adsorbed product and liophilizing the eluate containing the desired product (U.S. Pat. No. 4,313,875). However, the amorphous $N^4$-methyl-D-asparaginylamoxicillin anhydrate obtained by the known method gradually moistens in an ambient atmosphere and it is not stable unless it is stored by protecting from moisture and light.

It has now been found that $N^4$-methyl-D-asparaginylamoxicillin can be obtained in the form of a crystalline trihydrate. The new trihydrate of $N^4$-methyl-D-asparaginylamoxicillin is of superior quality in terms of its crystallinity and stability. In particular, the new trihydrate has been found to have a well-defined crystalline structure and it has been found to be remarkably stable in storage. These properties render the trihydrate of $N^4$-methyl-D-asparaginylamoxicillin of value in pharmaceutical use.

According to the present invention, $N^4$-methyl-D-asparaginylamoxicillin trihydrate can be prepared by adjusting the pH of a solution of $N^4$-methyl-D-asparaginylamoxicillin or a salt thereof in an aqueous medium to 3 to 6 and crystallizing the desired trihydrate.

Figure 1:
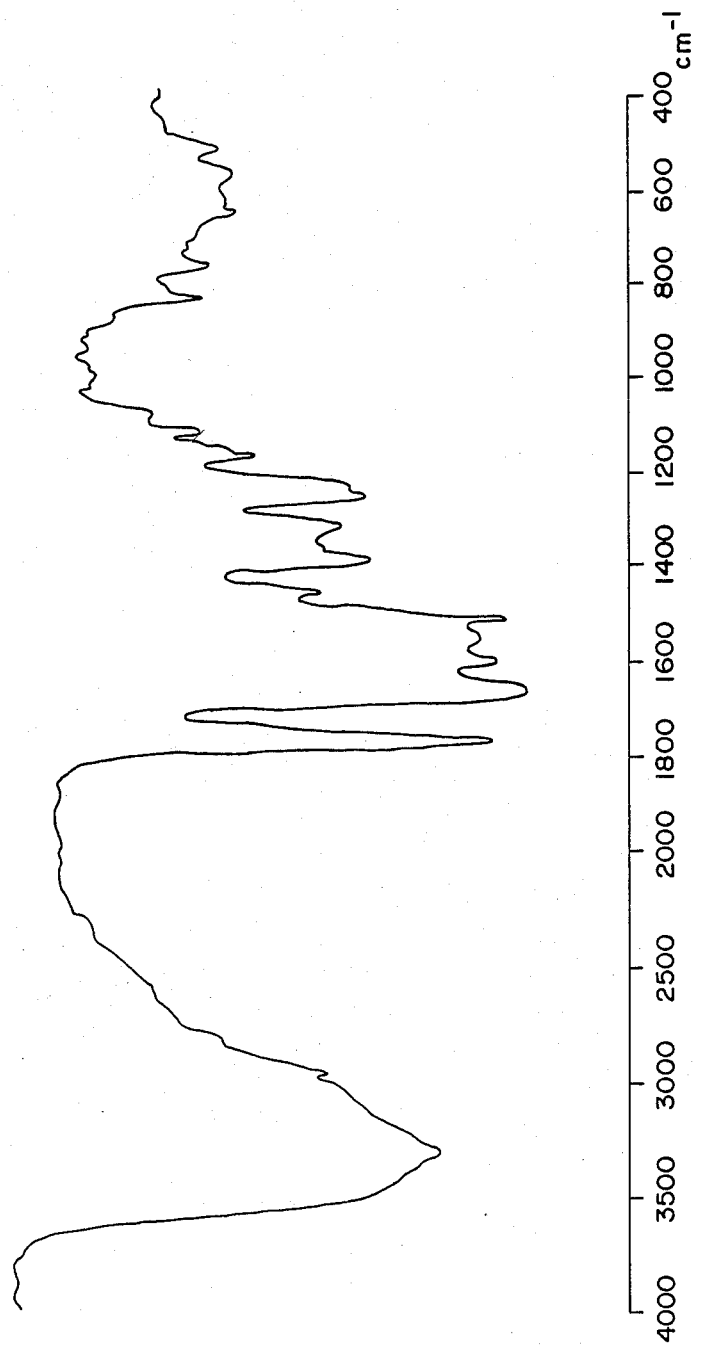
FIG. 1 is IR spectrum of the product obtained in Example 1.

DETAILED DESCRIPTION OF THE INVENTION $N^4$-Methyl-D-asparaginylamoxicillin to be used in the present invention may be either a crude product prepared by the method described in U.S. Pat. No. 4,053,609 or an amorphous anhydrate prepared by the method described in U.S. Pat. No. 4,313,875. Examples of the salt of $N^4$-methyl-D-asparaginylamoxicillin include alkali metal salts (e.g., sodium or potassium salt), alkaline earth metal salts (e.g., calcium or magnesium salt), amino acid salts (e.g., L-lysine, L-arginine, L-histidine or L-ornithine salt) or the salts with organic bases (e.g., triethylamine, tributylamine or N-methylmorpholine). Water, aqueous lower alkanols (e.g., aqueous methanol, aqueous ethanol or aqueous propanol) and aqueous lower alkanones (e.g., aqueous acetone or aqueous methylethylketone) are preferably used as the aqueous medium. From an industrial view-point, water is the most preferable as the aqueous medium.

In carrying out the method of the present invention, the solution of $N^4$-methyl-D-asparaginylamoxicillin or a salt thereof in the aqueous medium is firstly adjusted to a pH of 3 to 6, preferably 3.5 to 5.5. For example, when $N^4$-methyl-D-asparaginylamoxicillin is employed in the form of its free form, the adjustment of pH is carried out by adding an acid or an alkali to the solution of said compound. When $N^4$-methyl-D-asparaginylamoxicillin is employed in the form of its salt, the adjustment of pH is carried out by adding an acid to the solution of said salt. Examples of the acid to be used for the pH adjustment include a mineral acid such as hydrochloric acid or sulfuric acid or an organic acid such as citric acid, and examples of the alkali include an alkali metal hydroxide such as sodium hydroxide or potassium hydroxide. After the solution of $N^4$-methyl-D-asparaginylamoxicillin or its salts is adjusted to the prescribed pH, the desired trihydrate is crystallized from said solution. The crystallization of the desired trihydrate may be preferably conducted by cooling or condensation of the solution, or by addition of a water-miscible organic solvent, or by a combination thereof. For example, when the crystallization is carried out by cooling the solution, it is preferred that the solution which has previously been warmed to about 30° to 70° C. is cooled to 0° to 10° C. When the crystallization is carried out by condensation, it is preferred that the solution of $N^4$-methyl-D-asparaginylamoxicillin or its salt is condensed until the concentration of said compound is 10 to 45 w/w %, especially about 30 to 40 w/w %. Further, when the crystallization is carried out by the addition of a water-miscible organic solvent, said water-miscible organic solvent may be added intermittently or continuously to the solution of $N^4$-methyl-D-asparaginylamoxicillin or it salt. Examples of such water-miscible organic solvent include a lower alkanol such as methanol, ethanol or propanol, and a lower alkanone such as acetone or methylethylketone. The precipitated trihydrate can be readily separated by a conventional solid-liquid separation technique such as filtration or centrifugation.

As mentioned hereinbefore, $N^4$-methyl-D-asparaginylamoxicillin trihydrate of the present invention is difficult to moisten in an ambient atmosphere and is stable in storage. Therefore, said trihydrate is superior to the known amorphous anhydrate as bulk substance for medicine. Moreover, the trihydrate of the present invention is easy to handle because the bulk density and electrification thereof is less than those of the known amorphous anhydrate. Further, the trihydrate of the present invention is characterized in that it can be readily prepared in an industrial scale because of its good crystallinity.

EXPERIMENT (Stability test)

Each of crystalline $N^4$-methyl-D-asparaginylamoxicillin trihydrate of the present invention and amorphous $N^4$-methyl-D-asparaginylamoxicillin anhydrate (prepared according to the method described in U.S. Pat. No. 4,313,875) was allowed to stand at 40° C. in a sealed tube for 5, 10, 15 or 30 days, and the stability of each compound was estimated by measuring the content of $N^4$-methyl-D-asparaginylamoxicillin. The results are shown in the following Table 1.

The content of $N^4$-methyl-D-asparaginylamoxicillin was measured by high performance liquid chromatography (HPLC) under the conditions mentioned below.

[Conditions]

Column: Octadecylsilane (4.6 mm$\phi \times$150 mm)
Mobile phase: Phosphate buffer - acetonitrile (87:13) (pH:3.0)
Flow speed: 1.0 ml/minute
Temperature of column: 40° C.

Remaining ratio (%) of $N^4$—methyl-D-asparaginylamoxicillin =

$$\left[ \frac{\text{Content of } N^4\text{—methyl-D-aspara-ginylamoxicllin after it was allowed to stand}}{\text{Content of } N^4\text{—methyl-D-aspara-ginylamoxicillin before it was allowed to stand}} \right] \times 100$$

TABLE 1

| Test compound Nos. | Remaining ratio of $N^4$—methyl-D-asparaginylamoxicillin (%) A period of time during which the test compound was allowed to stand (days) | | | | |
|---|---|---|---|---|---|
| | Initial | 5 | 10 | 15 | 30 |
| 1. | 100.0 | 100.0 | 100.0 | 100.0 | 99.5 |
| 2. | 100.0 | 91.0 | 90.0 | 88.5 | 85.5 |

Test compound

1. Crystalline $N^4$-methyl-D-asparaginylamoxicillin trihydrate (The compound of the present invention)
2. Amorphous anhydrate of $N^4$-methyl-D-asparaginylamoxicillin (prepared according to U.S. Pat. No. 4,313,875)

EXAMPLE 1

Amorphous $N^4$-methyl-D-asparaginylamoxicillin anhydrate (10 g) is dissolved at 40° C. in water (50 ml). The solution is adjusted to pH 4.0 with diluted hydrochloric acid and stirred at 30° C. for one hour and then cooled to 5° C. The resultant precipitates are collected by filtration, washed with water and dried, whereby $N^4$-methyl-D-asparaginylamoxicillin trihydrate (8 g) is obtained as a white crystalline solid.

Water content (Karl Fisher Method): 10.05% (corresponds to 3 moles)
Content of product (HPLC): 99.7%
$[\alpha]_D^{20} + 179.5°$ (c=1.0, water)
Infrared spectrum: shown in FIG. 1
X-ray powder diffraction pattern: shown in the following Table 2
(Power source; Cu:Ni, 40KV, 35mA, $\lambda = 1.5405$)

Just for reference, the X-ray powder diffraction pattern of amorphous $N^4$-methyl-D-asparaginylamoxicillin anhydrate is also shown in Table 2.

TABLE 2

| Crystalline $N^4$—methyl-D-asparaginylamoxicillin trihydrate | | Amorphous $N^4$—methyl-D-asparaginylamoxicillin anhydrate | |
|---|---|---|---|
| 'd' value | Relative intensity* | 'd' value | Relative intensity* |
| 15.77 | w | 5.94 | vw |
| 10.77 | w | 5.50 | vw |
| 9.21 | vw | 4.57 | vw |
| 7.89 | w | | |
| 5.98 | s | | |
| 5.57 | vs | | |
| 5.34 | w | | |
| 4.98 | vw | | |
| 4.62 | vs | | |
| 4.39 | w | | |
| 4.23 | m | | |
| 3.97 | m | | |
| 3.77 | vw | | |
| 3.64 | vw | | |
| 3.54 | w | | |
| 3.48 | w | | |
| 3.37 | w | | |
| 3.25 | m | | |
| 3.13 | vw | | |
| 3.01 | w | | |
| 2.86 | vw | | |
| 2.81 | vw | | |
| 2.65 | vw | | |
| 2.60 | vw | | |
| 2.40 | w | | |

*The relative intensities were estimated by comparing the line intensities against a set of standards:
vs = very strong, s = strong, m = medium, w = weak, vw = very weak

EXAMPLE 2

Amorphous $N^4$-methyl-D-asparaginylamoxicillin anhydrate (10 g) is dissolved in water (500 ml) [The pH of the solution is 4.3]. The solution is concentrated under reduced pressure to 250 g, and ethanol (250 g) is added thereto. The resultant precipitates are collected by filtration and dried, whereby $N^4$-methyl-D-asparaginylamoxicillin trihydrate (5 g) is obtained as a white crystalline solid.

Water content (Karl Fisher Method): 10.74% (corresponds to 3 moles)
Content of product (HPLC): 99.3%
8 $[\alpha]_D^{20} + 179.3°$ (c=1.0, water)

EXAMPLE 3

Water (70 ml) is added to amorphous $N^4$-methyl-D-asparaginylamoxicillin anhydrate (22.2 g), and an aqueous 20% sodium hydroxide solution (5.4 ml) is added dropwise thereto to dissolve said anhydrate therein. Activated charcoal is added to the solution, and the mixture is filtered. The filtrate is adjusted to pH 3.5 with 20% hydrochloric acid (about 5.5 ml). The resultant precipitates are collected by filtration and dried, whereby $N^4$-methyl-D-asparaginyl by amoxicillin trihydrate (17 g) is obtained as a white crystalline solid.

Water content (Karl Fisher Method): 10.21% (corresponds to 3 moles)
Content of product (HPLC): 99.7%
$[\alpha]_D^{20} + 179.9°$ (c=1.0, water)

EXAMPLE 4

Thiobenzamide (20.5 g) is dissolved in ethanol (290 ml), and (2S, 5R, 6R)-6-{(2R)-2[(2R)-2-(o-nitrophenylsulfenyl)amino-3-(N-methylcarbamoyl)propionamido]-2-(p-hydroxyphenyl)acetamido}-3,3-dimethyl-7-oxo-4-thia-1-azabicyclo[3.2.0]heptane-2-carbosylic acid trihydrate (32.21 g) is added thereto. The mixture is stirred at 15° to 20° C. for 17 hours to remove the amino-protecting group (i.e., o-nitrophenylsulfenyl group). The precipitates (i.e., $N^4$-methyl-D-asparaginylamoxicillin) are collected by filtration, dried and then added to a suspension of activated charcoal (3 g) in water (50 ml). The suspension is adjusted to pH 5.5 with 1% hydrochloric acid (about 3 ml) and stirred at room temperature for one hour. Insoluble materials ar filtered off, and the filtrate is concentrated under reduced pressure until the concentration of $N^4$-methyl-D-asparaginylamoxicillin is 40 w/w %. The concentrated solution is stirred at 30° C. for one hour and then cooled to 5° C. The resultant precipitates are collected by filtration and dried, whereby $N^4$-methyl-D-asparaginylamoxicillin trihydrate (12.5 g) is obtained as a white crystalline solid.

Water content (Karl Fisher Method): 10.1% (corresponds to 3 moles)
Content of product (HPLC): 99.7%
$[\alpha]_D^{20} + 180.0°$ (c=1.0, water)

What we claim is:
1. (2S, 5R, 6R)-6-{(2R)-2[(2R)-2-Amino-3-(N-methylcarbamoyl)propionamido]-2-(p-hydroxyphenyl)acetamido}-3,3-dimethyl-7-oxo-4-thia-1-azabicyclo[3.2.0]heptane-2-carboxylic acid trihydrate.

* * * * *